United States Patent [19]

Stuart

[11] Patent Number: 4,658,833
[45] Date of Patent: Apr. 21, 1987

[54] MONITORING OF DRUG LEVELS

[76] Inventor: James F. B. Stuart, 1 Seafield Avenue, Bearsden, Glasgow G61 3LB, Scotland

[21] Appl. No.: 585,972

[22] Filed: Mar. 5, 1984

[30] Foreign Application Priority Data

Mar. 8, 1983 [GB] United Kingdom ............... 8306353

[51] Int. Cl.$^4$ ................................................ A61B 5/14
[52] U.S. Cl. ................................................ 128/771
[58] Field of Search ............... 128/764, 771, 762, 645, 128/646, 647, 648, 760, 743, 759, 635, 636; 252/408.1, 19, 8; 422/58; 604/317, 318, 890-894

[56] References Cited

U.S. PATENT DOCUMENTS

| | | | |
|---|---|---|---|
| 3,036,894 | 5/1962 | Forestiere | 422/58 |
| 3,266,868 | 8/1966 | Harvill | 128/771 |
| 3,509,872 | 5/1970 | Truhan | 128/771 |
| 3,769,961 | 11/1973 | Fatt et al. | 128/635 |
| 4,164,559 | 8/1979 | Miyata et al. | 604/894 |
| 4,184,491 | 1/1980 | McGannon | 128/760 |
| 4,190,060 | 2/1980 | Greenleaf et al. | 128/760 |
| 4,329,999 | 5/1982 | Phillips | 128/760 |
| 4,426,451 | 1/1984 | Columbus | 422/58 |

Primary Examiner—William E. Kamm
Attorney, Agent, or Firm—Leydig, Voit & Mayer

[57] ABSTRACT

The present invention provides a method of determining the concentration of a selected drug in the body of a subject comprising the steps of holding a liquid collecting means comprising an absorbent substantially inert member 1 in a position in close proximity to an eye 4 of the patient for collecting the fluid 7 therefrom; allowing the tear fluid collected to come into contact with reagent means 3 for reacting with said selected drug so as to produce, after a predetermined time interval, a physically detectable change dependent, at least semi-quantitatively, upon the concentration of said drug; and determining the physical change in said reactive portion after a predetermined interval of time.

6 Claims, 5 Drawing Figures

U.S. Patent   Apr. 21, 1987   Sheet 1 of 2   4,658,833
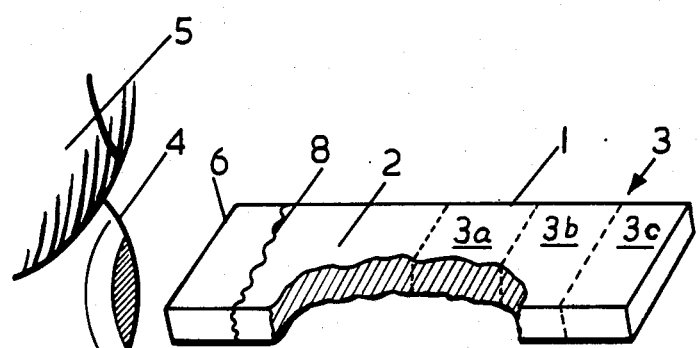
FIG. 1
FIG. 1A
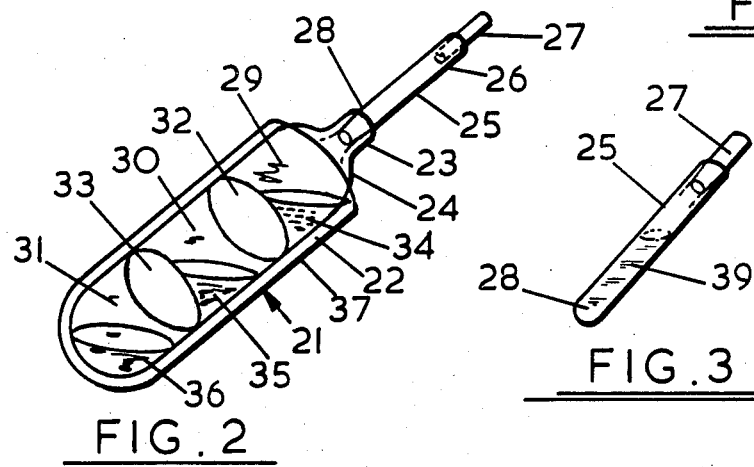
FIG. 2
FIG. 3

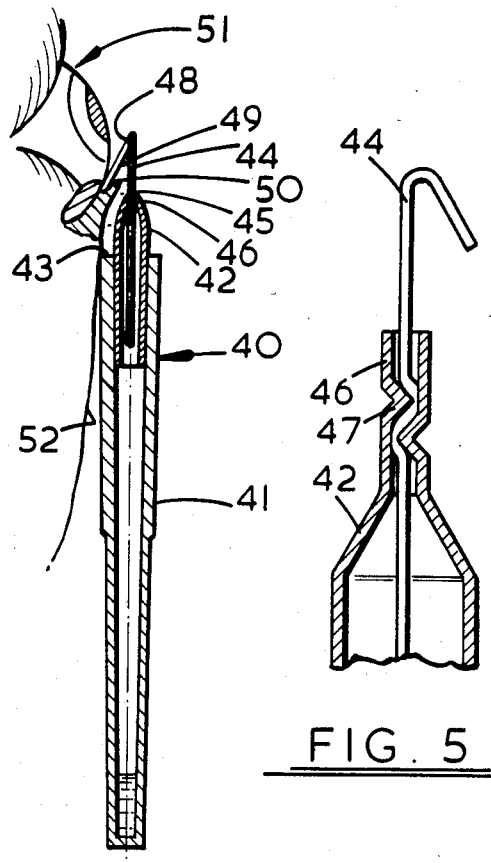

MONITORING OF DRUG LEVELS

The present invention relates to the monitoring of drug levels in the human body. Conventionally this is carried out by collecting samples of body fluid such as blood or urine and then carrying out a laboratory analysis thereof. Such a procedure whilst affording a high degree of accuracy can however entail considerable delays during transfer from the patient's bedside and in processing in the laboratory.

In practice there is often a need for a much more rapid method which whilst being at least semi-quantitative need not be fully accurate and which can be carried out at the bedside. In this connection there are available diagnostic materials in the form of a small absorbent pad impregnated with a chemical reagent and supported on a stick of impermeable material. The pad is dipped into a urine sample and the reagent changes colour according to the pH of the sample or the concentration of a particular metabolite or other material such as sugar or albumin with which the reagent reacts. Urine however is generally a rather complex mixture and often contains not only the material under investigation but also various metabolites thereof as well as many other materials.

It is therefore an object of the present invention to avoid or minimize one or more of the above disadvantges.

The present invention provides a method of determining the concentration of a selected drug in the body of a subject comprising the steps of holding a liquid collecting means comprising an absorbent substantially inert member in a position in close proximity to an eye of the patient for collecting tear fluid therefrom; allowing the tear fluid collected to come into contact with reagent means for reacting with said selected drug so as to produce, after a predetermined time interval, a physically detectable change dependent, at least semi-quantitatively, upon the concentration of said drug; and determining the physical change in said reactive portion after a predetermined interval of time.

As used herein the expression "inert member" is used to indicate a member which is substantially physiologically acceptable and does not contain any toxic material which could diffuse into tear fluid on or in the eye.

The liquid collecting means preferably comprises a deformable though more or less dimensionally stable absorbent material such as for example a strip of filter paper or stick of natural or synthetic fibrous material which can be readily held in a desired position in close proximity to a subject's eye without the danger of doing any physical damage thereto should it accidentally come into contact therewith.

Conveniently the liquid collecting means inert absorbent member is connected to an absorbent member containing said reagent means so as to allow diffusion of tear fluid from said inert absorbent member to the reagent containing one. Most conveniently said members are formed integrally as a single strip with respective adjoining inert and reactive portions.

In a preferred form of the invention though at least part of the tear fluid collected by the absorbent member is added to a quantity of said reagent means contained in a reaction chamber. Where the reagent means comprises a plurality of successively reacting reagents, these are conveniently contained in respective compartments of a multi-chamber vessel separated by breakable wall means.

Various reagents may be used in the reactive portion depending on the identity of the selected drug, the degree of specificity with respect to reaction with the selected drug, the type of physical change required and other factors. In general it is desirable though to use a reagent which produces a visually detectable colour change dependent upon the concentration of the selected drug present in the tear fluid.

In one preferred aspect the present invention provides a test strip suitable for use in a method of determining the concentration of a selected drug in the body, said strip having adjoining absorbent reactive and substantially inert portions, said reactive portion containing reagent means for reacting with said selected drug so as to produce, after a predetermined time interval, a physically detectable change in said reactive portion dependent at least semi-quantitatively, upon the concentration of said drug in a body fluid, said absorbent reactive and insert portions being capable of absorbing a body fluid in the inert portion and allowing diffusion thereof across the inert portion into and across the reactive portion.

With the present invention it is possible, using appropriate chemical reagent means to readily obtain an indication of the level of a drug in the body of a patient directly at the bedside in a simple and essentially, non-invasive manner. Whilst the above test strip is used with particular advantage and convenience in relation to tear fluid, it may be possible also to use it with other body fluids such as blood or urine.

Further preferred features and advantages of the invention will appear from the following detailed description given by way of example of a preferred embodiment illustrated with reference to the accompanying drawing in which:

FIG. 1 is a partially cut-away perspective view on an enlarged scale of a test strip of the invention, in use, in proximity to an eye and a reference card;

FIG. 2 is a perspective view of a second device of the invention;

FIG. 3 is a similar view of part of the device of FIG. 2;

FIG. 4 is a partly sectional elevation of a third device in use; and

FIG. 5 is a detail view of FIG. 4 on an enlarged scale.

FIG. 1 shows a test strip 1 for use in determining the level of paracetamol in the body. The strip is in the form of an elongate strip of white filter paper having a first, nonreactive, zone 2 which is substantially free of any added matter and a second, reactive, zone 3 containing a first section adjacent the non-reactive zone 2 for receiving 2N Hydrochloric Acid and then second and third adjoining sections impregnated respectively with 10% w/v aqueous sodium nitrite and the second impregnated with 4N aqueous sodium hydroxide.

In use the non-reactive or inert zone 2 of the strip 1, which zone is formed so as to be physiologically acceptable and free of the reagent and any other extraneous matter, is held close against the eye 4 of a patient 5 so that its free end 6 dips into tear fluid 7. The strip 1 is held in position for a predetermined period of time to collect sufficient tear fluid to infiltrate both the inert and reactive zones 2, 3, the tear fluid diffusing progressively through the strip 1 with the fluid front 8 advancing from the free end 6 across the inert zone into the reactive zone.

The strip is then removed from the eye and a few drops of 2N Hydrochloric Acid are added to the first section of the reactive zone 3 adjacent the nonreactive zone and preferably slightly spaced apart from the second section of the reactive zone 3. This is done in order to prevent prior mixing of the hydrochloric acid and the other reagents in the second and third sections before diffusion of the tear fluid through the acid to acidify the tear fluid. Diffusion of the tear fluid through the reactive zone 3 is allowed to proceed to completion. The strip is then surveyed visually and the colour of the reactive zone compared with a colour chart 10 having a plurality of zones 11 with different colours corresponding to different concentrations of paracetamol in the body.

In FIG. 2 is shown a device 21 of the invention wherein is used liquid reagent means held in a suitable container. Thus the device 21 of FIG. 2 comprises a vessel 22 of a generally dimensionally stable though deformable material for example a pliable inert plastics material, which is preferably transparent, which vessel 22 has an open neck 23 at one end 24. At the open neck 23 is provided a sample fluid collection chamber in the form of a narrow tube 25 having a first end 26 in which is fitted an absorbent member in the form of a small strip of filter paper 27 and which end 26 is formed and dimensioned for push-fit connection with the neck 23 of the main vessel 22 upon removal of the filter paper strip 27 after sampling. The second end 28 of the tube 25 is sealed.

The interior of the main vessel 22 is subdivided into three separate, first, second and third, compartments 29-31 isolated from each other by respective, first and second, wall means 32, 33 for containing first, second and third liquid reagents 34-35 of the reagent means (counting in each case away from the neck 23 of the main vessel 22). The wall means 32, 33 are formed of a somewhat more brittle material for example a suitable inert plastic material and/or with frangible portions so that by squeezing the main vessel around the wall means the wall means can be more or less readily broken through without impairing the liquid-tightness of the main vessel 22 itself. In order to protect the main vessel 22 against accidental breakage of the wall means 32, 33 the vessel 22 is desirably held in a removable substantially rigid casing 37 until breakage of the wall means is required or at least until immediately before use of the device.

In the present case the device is intended for use in assaying paracetamol and the first second and third reagents comprise, respectively, 2N Hydrochloric Acid (0.1 ml), 10% w/v aqueous Sodium Nitrite (0.1 ml), and 4N aqueous Sodium Hydroxide (0.1 ml).

In use of the device the tube 25 is detached from the main vessel 2. The filter paper strip 27 is brought up to the corner of a subject's eye and held there for a few minutes until sufficient tear fluid 39 has collected in the tube 25 having migrated through the filter paper strip 27. In order to determine the amount of tear fluid collected the tube 25 is, conveniently, graduated to show the volume of tear fluid therein.

The filter paper strip 27 is then removed from the first tube end 26 and the now open first end 26 of the tube 25 push-fitted to the vessel neck 23 taking care not to spill either tear fluid or hydrochloric acid—if desired an additional breakable wall means could be provided between the neck and the hydrochloric acid to facilitate the latter step, this wall means then being broken in the way as for the other wall means after the connection has been completed. If desired the tube 25 could be formed integrally with the main vessel 22 or permanently connected thereto though this alternative would be somewhat less preferred in order to exclude the possibility of any reagent coming into contact with the subject in any way.

The first wall means 32 is then broken to allow the sodium nitrite to react with the acidified acetaminophen (paracetamol)-containing tear fluid to form 2-Nitro-4-acetamidophenol. The second wall means is then broken to allow the sodium hydroxide to lower the pH so that the above reaction product is converted into an anionic form having an absorption maximum at a wavelength of 430 nm.

Various modifications may be made without departing from the scope of the present invention. Thus, for example, appropriate biochemical, for example enzyme-based, reagents could be used in place of chemical reagents as used in the above-described embodiments. Also other changes than in electromagnetic radiation absorption characteristics may be used to determine the reaction products including for example changes in electrical properties e.g. in electric potential. An example of the use of an enzyme-based reaction system for monitoring paracetamol concentrations will now be described.

FIG. 4 shows an alternative tear fluid collection system 40 comprising a narrow tubular vessel 41 having a tubular connector 42 in its open end 43. A strip of filter paper 44 is held at a central portion 45 in the free end 46 of the connector 42, for example with the aid of adhesive or by crimping 47 of the connector 42 around the strip 44 as shown in FIG. 5. The free end 48 of the strip is folded back over on itself so as to provide a generally hook shaped formation 49 which can be hooked over the bottom eyelid 50 the free end 48 of the strip 44 then being gripped between the eyeball 51 and the eyelid 50. With the patient in a generally recumbent position the relatively lightweight vessel 41 (conveniently made of an inert plastics material such as polyethylene) will rest naturally without the need for further support on the patient's cheek 52. After collection connection 42 is removed from vessel 41. A 50 l sample of tear fluid is mixed with 1.0 ml of buffered (pH 8.6 Tris HCl) aryl acylamide amidohydrolase enzyme in aqueous solution (containing 7 to 8 IU/l of the enzyme). The mixture was incubated at room temperature for 5 minutes and then 2 ml of colour reagent solution containing approximately 40 mmol/l o-cresol and 1 mmol/l copper sulphate in 30 mmol/l ammonia. The mixture was then allowed to stand at room temperature for 2 minutes and the absorbance thereof then read at 615 nm. (Further details of the reagent system are as disclosed in Clin. Chem. 29/2 358-361 (1983) by C. P. Price et al).

There will now be described an example of a suitable reagent system for use with another selected drug. 50 82 l of tear fluid is mixed with 100 $\mu$l of Ferric ammonium sulphate (2% w/v) in 2% v/v conc. HCL. Presence of salicylate in the tear fluid sample is indicated by development of a purple colour, the concentration present being ascertained by comparison with a standard colour chart. The sensitivity of the system allowed the distinguishing of 25 $\mu$g/ml concentration increments between 10 and 300 $\mu$g/ml and 50 $\mu$g/ml increments from 300 to 500 $\mu$g/ml.

In practice levels of salicylate below 100 $\mu$g may be ignored whilst levels above 100 $\mu$g/ml indicate the presence of therapeutic or toxic levels in the body in which case further more detailed testing may then be carried out by conventional methods to ascertain whether there is in fact a toxic level present.

It will be appreciated that the present invention is primarily concerned in indicating rapidly and easily at the bedside if necessary whether specific further more detailed tests require to be carried out rather than providing a particularly precise determination system.

In a further aspect the present invention provides a tear-fluid collection device comprising an elongate absorbent substantially inert member having one end portion formed and arranged into a generally hook-shaped structure which can be hooked over an eyelid of a subject with a free end portion inserted between said eyelid and the associated eyeball.

Various other drugs that may be monitored using the method and apparatus of the invention include bilirubin, methotrexate, phenobarbitone, gentomycin, theophylline, digoxin, and tricyclic antidepressants, the drug concentrations being determined with the aid of reagents comprising enzymes which react with the individual drugs concerned more or less specifically to produce a colour change.

What is claimed is:

1. A method of determining the concentration of a selected drug in the body of a subject comprising the steps of holding a liquid collecting means comprising an absorbent substantially inert member in a position in close proximity to an eye of the patient so as to contact surface tear fluid in the eye for collecting tear fluid therefrom; allowing the tear fluid collected to come into contact with reagent means for reacting with said selected drug so as to produce, after a predetermined time interval, a physically detectable change dependent, at least semi-quantitatively, upon the concentration of said drug; and determining the physical change in said reagent after a predetermined interval of time.

2. The method of claim 1 wherein the holding step comprises inserting and holding said member between the eyeball and eyelid of the subject, said member is in a form selected from the group consisting of a strip and a stick and comprises a fibrous material selected from the group consisting of natural and synthetic fibers.

3. The method of claim 2 wherein said collecting means has an absorbent member containing reagent connected thereto and said allowing step comprises diffusing said collected fluid into said reagent-containing means.

4. The method of claim 3 wherein said diffusing step includes placing the absorbent member in a reagent-containing vessel.

5. The method of claim 4 wherein said vessel comprises breachable wall means in said vessel forming plural compartments and at least first and second different reagents in different compartments, and said allowing step comprising bringing the tear fluid into contact with the first reagent, breaching the wall means and bringing the mixture of tear fluid and first reagent into contact with said second reagent.

6. The method of claim 1 wherein said physically detectable change is a visible color and said determining step comprises using a standard color reference for comparison with the color change by a process selected from the group consisting of spectrophotometry and direct visual comparison.

* * * * *